United States Patent
Gopalakrishnan et al.

(10) Patent No.: US 10,591,934 B2
(45) Date of Patent: Mar. 17, 2020

(54) MASS FLOW CONTROLLER FOR SUBSTRATE PROCESSING

(71) Applicant: Lam Research Corporation, Fremont, CA (US)

(72) Inventors: Sudhakar Gopalakrishnan, San Jose, CA (US); Peter Reimer, San Jose, CA (US); John Haruff, San Jose, CA (US); Dennis Smith, San Jose, CA (US)

(73) Assignee: Lam Research Corporation, Fremont, CA (US)

( * ) Notice: Subject to any disclaimer, the term of this patent is extended or adjusted under 35 U.S.C. 154(b) by 49 days.

(21) Appl. No.: 15/917,528

(22) Filed: Mar. 9, 2018

(65) Prior Publication Data
US 2019/0279888 A1    Sep. 12, 2019

(51) Int. Cl.
| | |
|---|---|
| *G05D 11/13* | (2006.01) |
| *G01F 1/84* | (2006.01) |
| *H01L 21/67* | (2006.01) |
| *G01N 9/32* | (2006.01) |

(52) U.S. Cl.
CPC ......... *G05D 11/137* (2013.01); *G01F 1/8468* (2013.01); *G01N 9/32* (2013.01); *G05D 11/139* (2013.01); *H01L 21/67253* (2013.01); *Y10T 137/2499* (2015.04); *Y10T 137/2504* (2015.04)

(58) Field of Classification Search
CPC .............. G05D 11/137; G05D 11/139; Y10T 137/2504; Y10T 137/2499; G01N 9/32; B01F 3/028; B01F 15/00233
See application file for complete search history.

(56) References Cited

U.S. PATENT DOCUMENTS

| | | | | | |
|---|---|---|---|---|---|
| 4,986,497 | A | * | 1/1991 | Susko | ....... B64F 5/20 137/88 |
| 5,447,744 | A | * | 9/1995 | Bryselbout | ....... B01J 4/008 137/4 |
| 5,455,076 | A | * | 10/1995 | Lee | ....... B01F 3/088 137/10 |
| 6,477,901 | B1 | * | 11/2002 | Tadigadapa | ....... G01F 1/8404 73/861.352 |
| 6,752,166 | B2 | * | 6/2004 | Lull | ....... G05D 7/0664 118/715 |
| 9,690,304 | B2 | * | 6/2017 | Downie | ....... G05D 11/137 |
| 2001/0032668 | A1 | * | 10/2001 | Doty | ....... G05D 11/132 137/93 |

(Continued)

*Primary Examiner* — Kevin F Murphy
(74) *Attorney, Agent, or Firm* — Penilla IP, APC (57) ABSTRACT

Methods and apparatuses for delivering a process gas to a processing chamber are provided. A mass flow controller includes a first flow line for introducing a process fluid and an inlet valve disposed along the first flow line for controlling a flow rate of the process fluid. The mass flow controller includes a second flow line for introducing a carrier fluid into the mass flow controller and a micro-electro-mechanical system (MEMS) Coriolis sensor for providing a density signal and a mass flow rate signal for a mixture of the process fluid and the carrier fluid. The mass flow controller provided includes an outlet valve for controlling a mass flow rate of the mixture that is output by the mass flow controller as well as a controller for operating the inlet valve based on the density signal and for operating the outlet valve based on the mass flow rate signal.

20 Claims, 8 Drawing Sheets

(56) References Cited

U.S. PATENT DOCUMENTS

2004/0141409 A1\* 7/2004 Breithaupt ................ B01F 3/08
366/152.2
2010/0031825 A1\* 2/2010 Kemp ................. B01F 3/04815
99/275

\* cited by examiner

MASS FLOW CONTROLLER FOR SUBSTRATE PROCESSING

BACKGROUND

1. Field of the Disclosure

The present embodiments relate generally to substrate processing systems, and, more particularly, to methods, systems, and computer programs for controlling fluid delivery to substrate processing systems.

2. Description of the Related Art

Substrate processing in semiconductor fabrication involves various processes such as deposition processes, etching processes, etc. Substrate processing is typically carried out in vacuum chambers where various gases are introduced for treatment of the substrate. Thermal or pressure based mass flow controllers may be used to control the mass flow rate of gases being introduced into substrate processing chambers. However, current mass flow controllers are not able to reliably control low gas flows that would be desirable for certain substrate processing steps.

It is in this context that embodiments arise.

SUMMARY

Methods, devices, systems, and computer programs are presented for controlling the flow of process gas that is delivered to a processing chamber. It should be appreciated that the present embodiments can be implemented in numerous ways, such as a method, an apparatus, a system, a device, or a computer program on a computer readable medium. Several embodiments are described below.

In one embodiment, a mass flow controller is provided. The mass flow controller includes a first flow line for introducing a process fluid into the mass flow controller and an inlet valve disposed along the first flow line for controlling a flow rate of the process fluid. The mass flow controller also includes a second flow line for introducing a carrier fluid into the mass flow controller and a micro-electro-mechanical system (MEMS) Coriolis sensor for providing a density signal and a mass flow rate signal for a mixture of the process fluid and the carrier fluid. Additionally, the mass flow controller includes an outlet valve for controlling a mass flow rate of the mixture that is output by the mass flow controller as well as a controller for operating the inlet valve based on the density signal and for operating the outlet valve based on the mass flow rate signal.

In another embodiment, a method is provided for controlling delivery of a process fluid. The method includes an operation for receiving, from a Coriolis sensor of a mass flow controller (MFC), a density signal and a mass flow rate signal for a mixture of the process fluid and a carrier fluid. The method also includes operations for calculating a fluid mix ratio of the mixture based on the density signal and for adjusting the flow of the process fluid entering the MFC based on the fluid mix ratio. Further, the method includes operations for calculating the mass flow rate of the mixture based on the mass flow rate signal and for adjusting an output flow rate of the mixture exiting the MFC based on the mass flow rate of the mixture.

In another embodiment, a mass flow controller is provided. The mass flow controller includes a mixing and sensing module for mixing a process fluid and a carrier fluid into a mixture, the mixing and sensing module provides a density signal and a mass flow rate signal for the mixture. The mass flow controller also includes an inlet valve for controlling a flow rate of process fluid entering the mixing and sensing module and an outlet valve for controlling an output flow rate of the mixture exiting the mixing and sensing module. Further, the mass flow controller includes a controller for calculating a fluid mix ratio of process fluid to carrier fluid based on the density signal and for calculating a mass flow rate of the mixture based on the mass flow rate signal for the mixture. According to these and other embodiments, the controller is configured for adjusting the inlet valve based on the fluid mix ratio and for adjusting the outlet valve based on the mass flow rate of the mixture.

Other aspects will become apparent from the following detailed description, taken in conjunction with the accompanying drawings.

BRIEF DESCRIPTION OF THE DRAWINGS

The embodiments may best be understood by reference to the following description taken in conjunction with the accompanying drawings.

DETAILED DESCRIPTION

Embodiments provide mass flow controllers for substrate processing in semiconductor fabrication. For certain substrate processing steps, a lower flow of a process gas is required, for example, a flow rate of roughly 2 standard cubic centimeters per minute (sccm) or lower. Processing steps that involve low flows of gas include deposition processes such as chemical vapor deposition (CVD), atomic layer deposition (ALD), as well as etching processes such as plasma etching and atomic layer etching (ALE). Current flow controllers, which include thermal-based flow meters and pressure-based flow meters, are not reliably able to control lower flows of gas (e.g., flows of about 2 sccms or lower).

For certain processing steps that involve low flows of a process gas, a larger flow of a carrier gas such as argon (Ar) may be used. In conventional processes, separate mass flow controllers for each of the process gas and the carrier gas are used to ensure accurate flows of the gases are provided to the processing chamber. The process gas and the carrier gas are mixed together at a mixing point before being delivered to the processing chamber.

Figure 1:
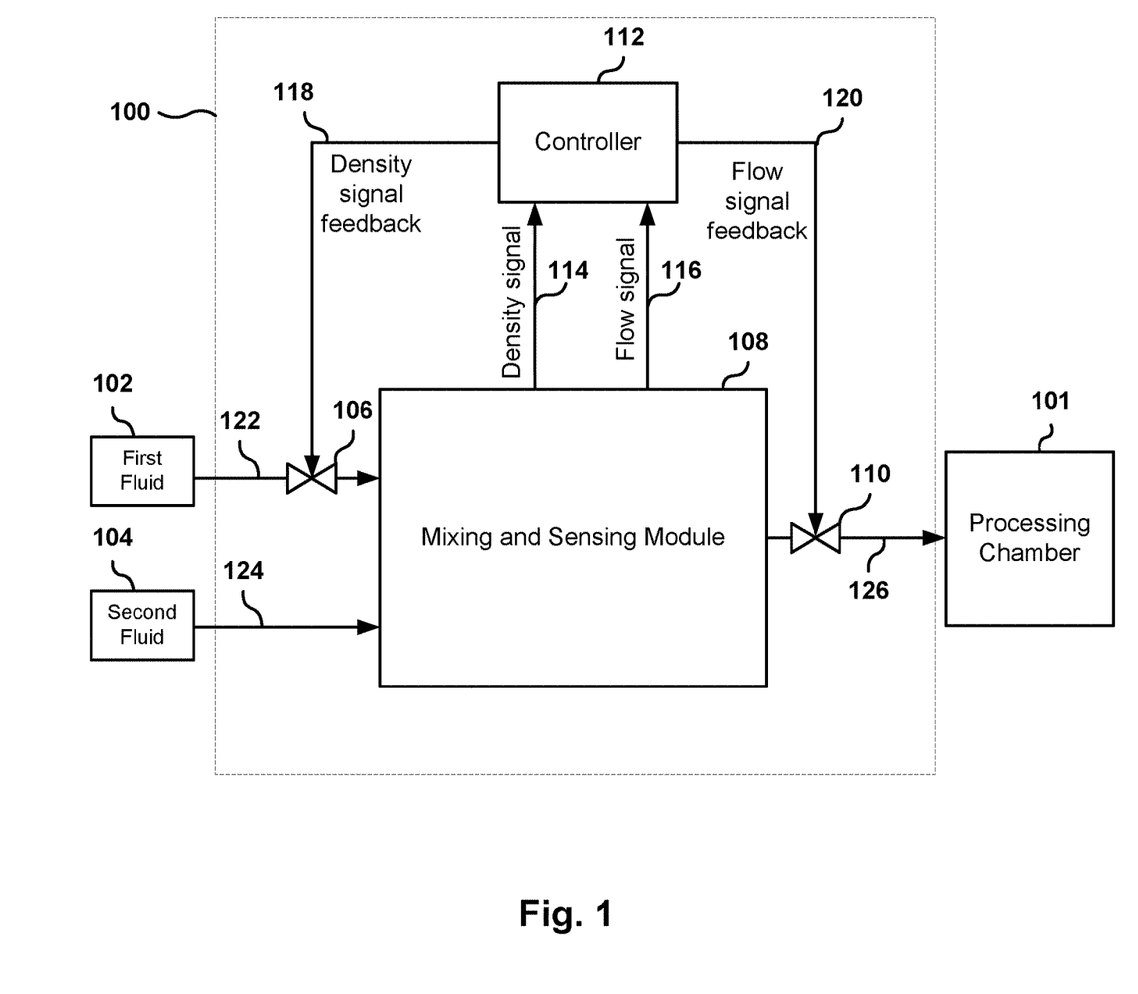
FIG. 1 is a schematic diagram of a system for controlling delivery of a mixture of a first fluid and a second fluid to a processing chamber, according to one embodiment.

Embodiments described herein include gas delivery systems and mass flow controllers (MFCs) that can measure, control, and deliver low flows of process gas (e.g., less than 2 sccms) within a mixture with carrier gas. Some of the embodiments described use one or more micro-electro-mechanical system (MEMS) based Coriolis sensors. In some embodiments, gas delivery systems are able to measure and control the respective mass flow rates of both the process gas and the carrier gas using a single mass flow controller. In these and other embodiments, the gas delivery systems are able to ensure that an accurate amount of process gas is being delivered to the processing chamber even when the flow rate of the process gas is relatively low (e.g., less than about 2 sccms). As used herein, a low flow rate may include a range of flow rates of about 2 sccms or lower, FIG. 1 is a schematic diagram of a system for controlling delivery of a mixture of a first fluid and a second fluid to a processing chamber, according to one embodiment. The system shown includes a mass flow controller (MFC) 100 that controls delivery of a first fluid as supplied by first fluid supply 102 and a second fluid as supplied by second fluid supply 104 to a processing chamber 101. In various embodiments, the first fluid may include a process gas while the second fluid may include a carrier gas.

The first fluid supply 102 supplies the first fluid to the MFC 100 via flow line 122 and the second fluid supply 104 supplies the second fluid to the MFC 100 via flow line 124. An inlet valve 106 is disposed along flow line 122 for controlling a flow rate of the first fluid that is supplied to the MFC 100. In the embodiment shown in FIG. 2, an inlet valve for the carrier gas is not used to control the flow rate of the carrier gas because the MFC 100 is relatively unaffected by the flow rate of the carrier gas, as will be described in more detail below with reference to FIG. 6. In other embodiments, however, an inlet valve that is disposed along supply line 124 may also be included to control the flow rate of the carrier gas entering the MFC 100.

Both the first fluid and the second fluid are made to flow into a mixing and sensing module 108. The mixing and sensing module 108 serves to, among other functions, mix the first fluid and the second fluid into a mixture. For example, if the first fluid is a process gas and the second fluid is a carrier gas, the mixing and sensing module 108 will produce a mixture containing process gas along with carrier gas. The mixture exits the mixing and sensing module 108 via an outlet line 126 for introduction into the processing chamber 101. An outlet valve 110 disposed along outlet line 126 controls a total flow rate of the mixture that exits the MFC 100 and is introduced into the processing chamber 101.

In addition to mixing the first and second fluids, the mixing and sensing module 108 provides a density signal 114 and a flow signal 116 to a controller 112 of the MFC 100. The density signal 114 is related to respective densities of the first fluid, the second fluid, or a mixture of the first fluid and the second fluid. The controller 112 processes the density signal 114 into, for example, a density reading in terms of mass divided by volume (e.g., kg/m³ or g/L, or in any other units representing units of mass per units of volume).

According to the embodiment shown in FIG. 1, the controller 112 uses the density signal 114 to provide a density feedback signal 118 to control the inlet valve 106. The density feedback signal 118 is used to control a flow rate of the first fluid that is introduced into the MFC 100 via the supply line 122 for the first fluid. As a result, the density feedback signal 118 provided by controller 112 is able to control a proportion of first fluid that is mixed in with the second fluid. For example, the density feedback signal 118 is able to control a fractional density of the first fluid of the mixture between the first fluid and the second fluid.

According to the embodiment shown in FIG. 1, the mixing and sensing module 108 also provides a flow signal 116 that is related to the respective flow rates of the first fluid, the second fluid, or a mixture of both the first fluid and the second fluid. The flow signal 116 is processed by the controller 112 to obtain a flow rate measurement for the mixture in terms of volume divided by time (e.g., standard cubic centimeters per minutes, or any other units representing units of volume per unit of time), or in terms of mass divided by time (e.g., g/minute, or g/hour, or any other unit representing units of mass per unit of time).

The controller 112 uses flow rate data provided by the flow signal 116 to generate a flow signal feedback 120 to control the outlet valve 110 for controlling a total flow rate of the mixture of the first and second fluids that exits the MFC 100 and that enters the processing chamber 101. Since the controller 112 controls the fractional density of both the first and second fluids in the mixture via the inlet valve 106, as well as the total flow rate of the mixture via the outlet valve 110, the MFC 100 is therefore able to precisely and accurately control the true mass flow rate(s) of first fluid and/or the second fluid that are introduced into the processing chamber 101.

For example, if the first fluid is a process gas and the second fluid is a carrier gas, the MFC 100 shown in FIG. 1 is able to control the fractional density of the process gas with respect to the mixture by way of the inlet valve 106. That is, for example, the MFC 100 is enabled to create a mixture having a desired proportion or ratio of process gas to carrier gas, even when the flow of process gas through flow line 122 is low, e.g., 2 sccms or lower. Moreover, the MFC 100 is also able to control the flow rate of the mixture having the desired proportion of process gas to carrier gas via outlet valve 110, and as a result, is able to control precisely and accurately the true mass flow rate of the process gas that is introduced into the processing chamber 101.

Figure 2:
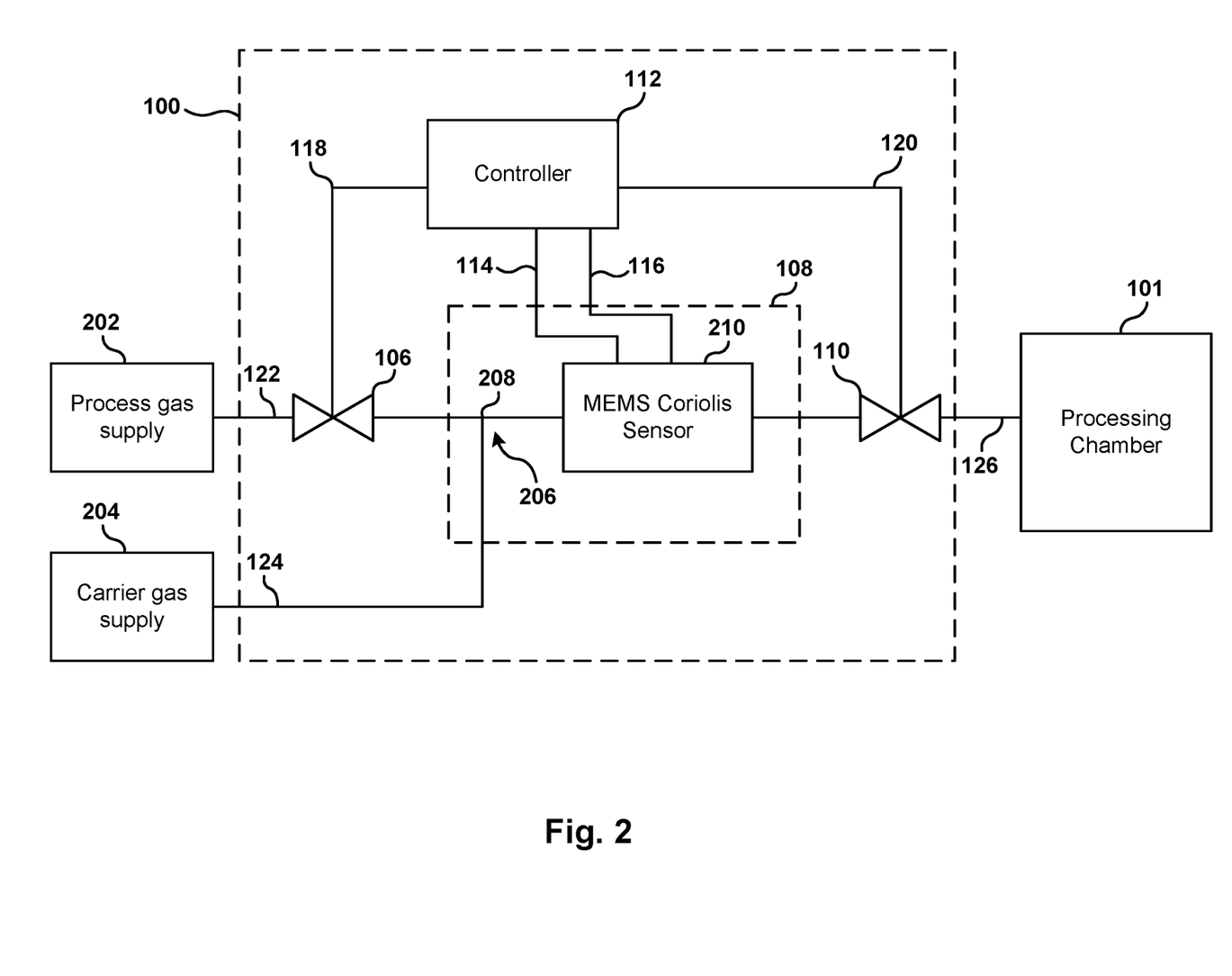
FIG. 2 is a schematic diagram of a system for controlling delivery of a mixture of a process gas and a carrier gas to a processing chamber using a single Coriolis sensor, according to one embodiment.

In some embodiments, the mixing and sensing module 108 shown in FIG. 1 may include a single sensor that provides a density signal 114 and a flow signal 116. FIG. 2 shows an embodiment of an MFC 100 having a mixing and sensing module that uses a single micro-electro-mechanical system (MEMS)-based Coriolis sensor (or, simply MEMS Coriolis sensor) for obtaining the density signal 114 and the flow signal 116 for a mixture of the first and second fluids. In other embodiments, the mixing and sensing module 108 may include two or more sensors that provide the density signal 114 and the flow signal 116. For example, in FIG. 3, an MFC 100 is shown to include a first MEMS-based Coriolis sensor for a process gas and a second MEMS-based Coriolis sensor for a carrier gas.

FIG. 2 is a schematic diagram of a mass flow controller (MFC) 100 that is in fluid communication with a processing chamber 101, according to one embodiment. The MFC 100 supplies the processing chamber 101 with a mixture of a process gas supplied by a process gas supply 202 and a carrier gas supplied by a carrier gas supply 204. The mixture may be introduced into the processing chamber 101 via a showerhead, a gas distribution ring, or any other suitable delivery arrangement (not shown). As noted above, the mixture introduced into the processing chamber 101 may be used for various processing steps that include, as non-delimiting examples, plasma etching, chemical etching, atomic layer etching (ALE), chemical vapor deposition (CVD), atomic layer deposition (ALD), etc.

According to the embodiment shown in FIG. 2, the MFC 100 receives the process gas from process gas supply 202 via flow line 122 and the carrier gas from carrier gas supply 204 via flow line 124. An inlet valve 106 is disposed along flow line 122 and controls the flow rate of the process gas that is introduced into the MFC 100. The inlet valve 106 may be any type of flow restriction device such as a fixed orifice or a needle valve or the like. The inlet valve 104 is capable of providing a flow range of about 0 sccm to about 10 sccms, or about 0.1 sccms to about 2 sccms, to suit the needs of various applications. In some embodiments, the flow rate of the carrier gas may be higher than that of the process gas, for example, by about 2-fold to about 100-fold or more. Thus, in various embodiments, the carrier gas in supply line 124 may have a flow rate of between 1 sccms to about 200 sccms, or between about 2 sccms to about 20 sccms.

According to the embodiment shown in the FIG. 2, the flow lines 122 and 124 enter the mixing and sensing module 108 where the contents of the flow lines 122 and 124 are mixed and measured for a density signal 114 and a flow signal 116. More particularly, the flow line 122 carrying the process gas and the flow line 124 carrying the carrier gas connect at a connector 208. The connector 208 serves as the mixing point 206 where the process gas mixes into and with the carrier gas to form a mixture. The connector 208 may be any type of suitable connector or coupling that connects flow lines 122 and 124.

In the embodiment shown in FIG. 2, the inlet valve 106 is shown to be disposed downstream of the process gas supply 202 but upstream of the connector 208 and mixing point 206. As a result, the inlet valve 106 controls the flow rate of only the process gas and not the flow rate of the carrier gas. It is noted that an optional inlet valve for the carrier gas may be disposed along flow line 124 upstream of the connector 208 and mixing point 206 in order to control the flow rate of the carrier gas. However, such an inlet valve for controlling the flow rate of the carrier gas may not be necessary in some embodiments because the MFC 100 is relatively unaffected by the precise flow rate of carrier gas into the MFC as along as the flow rate is within an operational range. In some embodiments, the operational flow range of the carrier gas is between about 1 sccms and about 200 sccms, or between about 2 sccms and about 50 sccms, or between about 5 sccms to about 15 sccms, depending on various applications.

From connector 208 and mixing point 206, the mixture then enters a MEMS Coriolis sensor 210. The MEMS Coriolis sensor 210 provides a density signal 114 and a flow signal 116 to controller 112. The density signal 114 will be related to a density of the mixture of the process gas and the carrier gas from which a ratio of the process gas to the carrier gas may be obtained. The flow rate signal 116 is related to the mass flow of the mixture that enters the MEMS Coriolis sensor 210. Together, the density signal 114 and the flow signal 116 may be used to determine the true mass flow rate of, for example, the process gas specifically. In addition, the MFC 100 is able to control, via the inlet valve 106 and the outlet valve 110, the true mass flow rate of the process gas that is introduced into the processing chamber 101.

In one embodiment, the MEMS Coriolis sensor 210 is a micromachined Coriolis sensor that is capable of obtaining signals for both the mass flow rate of a fluid that flows through the sensor, as well as the density of the fluid. In some embodiments, the MEMS Coriolis sensor 210 will include a silicon-based tube that forms a curved loop, although other materials and other shapes may be used. The tube is then driven to a resonant frequency of oscillation or vibration. In some embodiments, the tube is driven electrostatically, while in other embodiments, the tube may be driven piezoelectrically or electromagnetically.

When a fluid is introduced into the tube, the resonant frequency of oscillation changes (e.g., decreases) due to the increased inertia associated with the tube and the contents of the tube. The change in resonant frequency of oscillation, $\Delta f_B$, is directly proportional to the density, $\rho$, of the fluid, as expressed in equation (1).

$$\Delta f_B \propto \rho \quad (1)$$

It is envisioned that the measurement of $\Delta f_B$ may be obtained with an accuracy such that the accuracy associated with density, $\rho$, is at least $10^{-5}$ $\Delta\rho/\rho$. As a result, the accuracy of the fluid density measurement provided by the MEMS Coriolis sensor 210 is precise enough to also be used for fluid identification.

When fluid travels through the curved loop, fluid that travels away from an axis of oscillation exerts a force on a first section of the curved loop that extends away from the axis of oscillation near the inlet of the curved loop. The force exerted back onto the fluid causes the fluid to experience an increase in angular momentum to match the angular momentum of the curved loop. As the fluid travels back toward the axis of oscillation through a second section of the curved loop that extends back toward the axis of oscillation near the outlet, the fluid exerts a force on the second section as its angular momentum is made to decrease. As a result, the first section of the curved loop experiences a negative phase shift relative to the central portion of the curved loop (e.g., the first section lags behind) whereas the second portion of the curved loop experiences a positive phase shift relative to the central portion of the curved loop (e.g., the second section oscillates ahead of the central portion of the curved loop). The degree of phase difference between the first portion and the second portion is directly proportional to the amount of mass that is flowing through the tube of the MEMS Coriolis sensor 210. The mass flow rate of a fluid through the MEMS Coriolis sensor 210 may be related to the phase shift or time lag as set forth in equation (2):

$$Q_m = \frac{K_u - I_u \omega^2}{2Kd^2} \tau \quad (2)$$

In equation (2), $K_u$ is the temperature dependent stiffness of the tube, K is a shape-dependent factor, d is the width of the curved loop, $\rho$ is the time lag, $\omega$ is the oscillation or vibration frequency, and $I_u$ is the inertia of the tube. The time lag $\omega$ may be measured in a number of ways, for example electrostatically, piezoelectrically, or electromagnetically. Moreover, the measurement in time lag $\omega$ may be measured with a degree of accuracy such that the measurement of mass flow rate $Q_m$ may be obtained with an accuracy of at least about $5 \times 10^{-4}$ $\Delta Q_m/Q_m$.

Using the density measurement of the fluid that is measured by examining $\Delta f_B$ associated with the density signal 114, the inertia $I_u$ may be calculated, resulting in an accurate reading of the true mass flow rate of the fluid traveling through the MEMS Coriolis sensor 114. Thus, the MEMS Coriolis sensor 210 is enabled to provide accurate signals such that accurate determinations of both the density and the mass flow rate of the process gas may be made by MFC 100.

In one embodiment, the MEMS Coriolis sensor 210 provides at least a density signal 114 and a flow signal 116 to the controller 112 of the MFC 100. The density signal 114 may include oscillation frequency measurements of the tube of the MEMS Coriolis sensor 210, while flow signal 116 may include phase shift or time lag information. Controller 112 processes the density signal 114 and the flow signal 116 to calculate the density and the mass flow rate of the fluid traveling through the MEMS Coriolis sensor 210. The controller 112 operates the inlet valve 106 based on the density signal 114 received from the MEMS Coriolis sensor 210 in order to adjust a ratio of process gas to carrier gas within the mixture that is delivered to the processing chamber 101. That is, for example, the controller 112 adjusts the fraction of the total density of the mixture that is measured by the MEMS Coriolis sensor 210 by adjusting the flow rate the process gas that enters the MFC 100.

The controller 112 also operates the outlet valve 110 in order to adjust the total mass flow of the mixture that is being delivered to the processing chamber 101. By controlling both the ratio of process gas within the mixture as well as the total mass flow of the mixture, the MFC 100 is able to accurately control a mass flow rate of the process gas specifically that is delivered to the processing chamber 101. The MFC 100 is able to accurately adjust a true mass flow rate of the process gas to a desired rate by separately adjusting the inlet valve 106 to adjust for the ratio of the process gas within the mixture, as well as by adjusting the total mass flow rate of the mixture that is introduced to the processing chamber 101.

The following describes one embodiment for determining the ratio of process gas to carrier gas and how such a determination may be used to achieve an accurate flow of process gas that is delivered to the processing chamber 101. When the inlet valve 106 is in some open state, a steady flow of process gas is mixed with a larger flow of carrier gas. As an example, the process gas may be chlorine ($Cl_2$) having a flow rate of about 1 sccm, while the carrier gas may be argon (Ar) having a flow rate of about 10 sccms. In this example, when a mixture of the chlorine and the argon enters the MEMS Coriolis sensor 210, the MEMS Coriolis sensor 210 may provide a density signal 114 that is associated with the mixture. The controller 112 may then calculate the density of the mixture to be about 2.00000 g/L, for example. As noted above, the density of a measured fluid may be calculated to an accuracy of $10^{-5}$, as is shown here, or greater. From this density reading the controller 112 or associated computing system may then calculate the ratio of the mixture, for example, by using the following expression:

$$\rho_m = x\rho_{Ar} + y\rho_{Cl_2} \quad (3)$$

where $\rho_m$ is the density measurement of the mixture, $\rho_{Ar}$ and $\rho_{Cl_2}$ are the densities for Ar and $Cl_2$, respectively, and x and y are the fractional densities of Ar and $Cl_2$ within the mixture, respectively, and where $x+y=1$. Both $\rho_{Ar}$ and $\rho_{Cl_2}$ may be found from a look-up table when pressure and temperature are known for the MEMS Coriolis sensor 210. Alternatively, density, $\rho$, may be calculated using, for example, the following relationship:

$$\rho = \frac{P}{R_{sp}T} \quad (4)$$

where P is the pressure within the tube of the MEMS Coriolis sensor 210, $R_{sp}$ is the specific gas constant for a gas, and T is the temperature of the gas. For the sake of clarity, assume that $\rho_{Ar}$ and $\rho_{Cl_2}$ are calculated or found to be $\rho_{Ar}=1.784$ g/L and $\rho_{Cl_2}=3.2$ g/L. Therefore, from equation (3), x will be found to be x=0.84745 and y will be found to be y=0.15255. Because the value for $\rho_m$ may be associated with a high degree of accuracy, the accuracy of the calculated density fractions of x and y may have similar high degrees of accuracy, depending upon the accuracy of the other variables shown in equation (4).

According to this example, if the fractional density of $Cl_2$ within the mixture of y=0.15255 is higher than a desired ratio, then the controller 112 may adjust the inlet valve 106 via density signal feedback 118 to reduce the flow of $Cl_2$ until the desired ratio is achieved. If the fraction density of $Cl_2$ within the mixture is lower than the desired ratio, then the controller 112 may adjust the inlet valve 106 to increase the flow of $Cl_2$ until the desired ratio is achieved via density signal feedback 118.

In some embodiments, control over the precise amount of process gas that is introduced into processing chamber 101 may be desired. One way to precisely control the amount of process gas that is introduced into the processing chamber 101 is to precisely control the mass flow rate of the process gas by way of precisely controlling the total flow rate of the mixture as well as the time that the mixture is allowed to flow into the processing chamber 101 (e.g., when the ratio of process gas within the mixture is known accurately). This may be the case, for example, in applications involving atomic layer deposition and/or etching. Continuing with the example described above, assume that the desired gas mix ratio has been met with x=0.84745 and y=0.15255. If the MEMS Coriolis sensor 210 provides a flow signal 116 that results in a mass flow calculation of argon-chlorine mixture of m=0.02000 g/min, then the mass flow rate of $Cl_2$ specifically may be calculated to be $$\dot{m}_{Cl_2} = y\dot{m}_{mixture} = 0.0030510 \; \frac{\text{g}}{\text{min}}.$$

Again, because the mass flow value may be determined with an accuracy of at least about $5 \times 10^{-4}$, the accuracy of the specific mass flow rate for $Cl_2$ may be similarly accurate.

If the mass flow rate of the process gas is higher than what is desired, the controller 112 may send a flow signal feedback 120 to the outlet valve 110 in order to reduce the total mass flow of the mixture exiting the MFC 100. If the mass flow rate of the process gas is lower than what is desired, the controller 112 may then send a flow signal feedback 120 to the outlet valve 110 to increase the total mass flow of the mixture that is introduced into the processing chamber 101. The aforementioned steps may be repeated until the desired mass flow rate of process gas is achieved. Alternatively, or in addition, the controller 112 may send a density signal feedback 118 to the inlet valve 106 in order to adjust the flow of process gas that enters into the MFC 100. In this manner, the ratio of the process gas may also be adjusted in parallel to adjusting the total mass flow rate of the mixture that enters the processing chamber 101.

As noted above, an optional second inlet valve (not shown) for the carrier gas may also be used to adjust the flow rate of the carrier gas that enters the MFC 100. However, it is noted that embodiments shown in FIG. 2 may be implemented without the inlet valve for the carrier gas because the density signal of the MFC 100 is relatively independent of the flow rate of the carrier gas. Moreover, the accuracy of both the density signal 114 and the flow signal 116 of the MFC 100 is relatively unaffected by the flow rate of the carrier gas. For example, the MFC 100 is contemplated to have an operational range with respect to the flow rate of carrier gas of about 1 sccm to about 100 sccms, or about 2 sccms to 20 sccms, or about 5 sccms to about 10 sccms.

Figure 3:
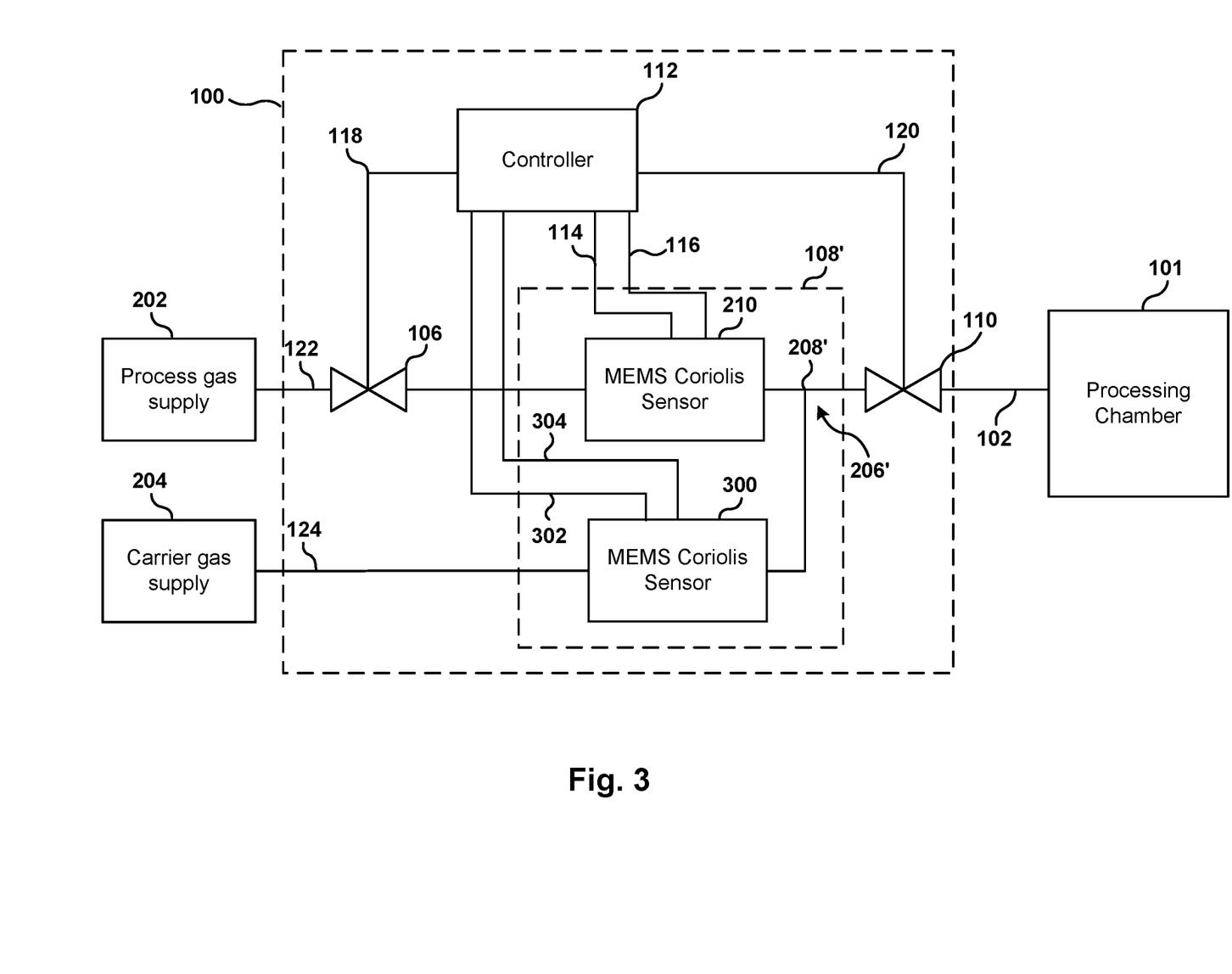
FIG. 3 is a schematic diagram of a system for controlling delivery of a mixture of a process gas and a carrier gas to a processing chamber using two Coriolis sensors, according to one embodiment.

FIG. 3 is a schematic diagram of a system for controlling delivery of a mixture of a process gas and a carrier gas to a processing chamber using two Coriolis sensors, according to one embodiment. In this embodiment, the mixing and sensing module 108' includes a MEMS Coriolis sensor 210 for the process gas that is supplied by the process gas supply 202 and a MEMS Coriolis sensor 300 for the carrier gas that is supplied by the carrier gas supply 204. Similar to the embodiment of FIG. 2, an inlet valve 106 is disposed along flow line 122 for controlling the flow rate of the process gas that enters the MFC 100. However, unlike the MFC 100 shown in FIG. 2, the mixing and sensing module 108' in the embodiment of FIG. 3 includes a MEMS Coriolis sensor 210 that provides a density signal 114 and a flow signal 116 specific to the process gas, while the MEMS Coriolis sensor 300 for the carrier gas provides a density signal 302 and a flow signal 304 that is specific to the carrier gas. Also unlike the mixing and sensing module 108 shown in FIG. 2, the mixing and sensing module 108' of FIG. 3 shows a connector 208' and a mixing point 206' that is downstream of the MEMS Coriolis sensors 210 and 300.

In the embodiment shown in FIG. 3, the density of the process gas and the density of the carrier gas may be obtained via the density signals 114 and 302, respectively. From these signals, the ratio of process gas to carrier gas may be calculated by controller 112. In addition, if the desired ratio of process gas to carrier gas is not met, the controller 112 may send a density signal feedback 118 to the inlet valve 106 in order to adjust the flow of process gas until the desired ratio is achieved.

Since flow signals 116 and 304 are obtained individually for the process gas and the carrier gas, the total mass flow of the mixture that results after the process gas and the carrier gas are mixed may be obtained by controller 112. In some embodiments, the total mass flow of the mixture is derived from the sum of the mass flow of the process gas and the mass flow of the carrier gas as provided by the flow signals 116 and 304, respectively. If the desired mass flow of the process gas entering the processing chamber 101 is higher or lower than a desired rate, the controller 112 may adjust outlet valve 110 via flow signal feedback 120 to achieve a desired total mass flow rate of the mixture. By adjusting the outlet valve 110 to achieve a desired total mass flow rate of the mixture, the desired mass flow rate of the process gas may also be achieved when the ratio of process gas to carrier gas is known.

Figure 4:
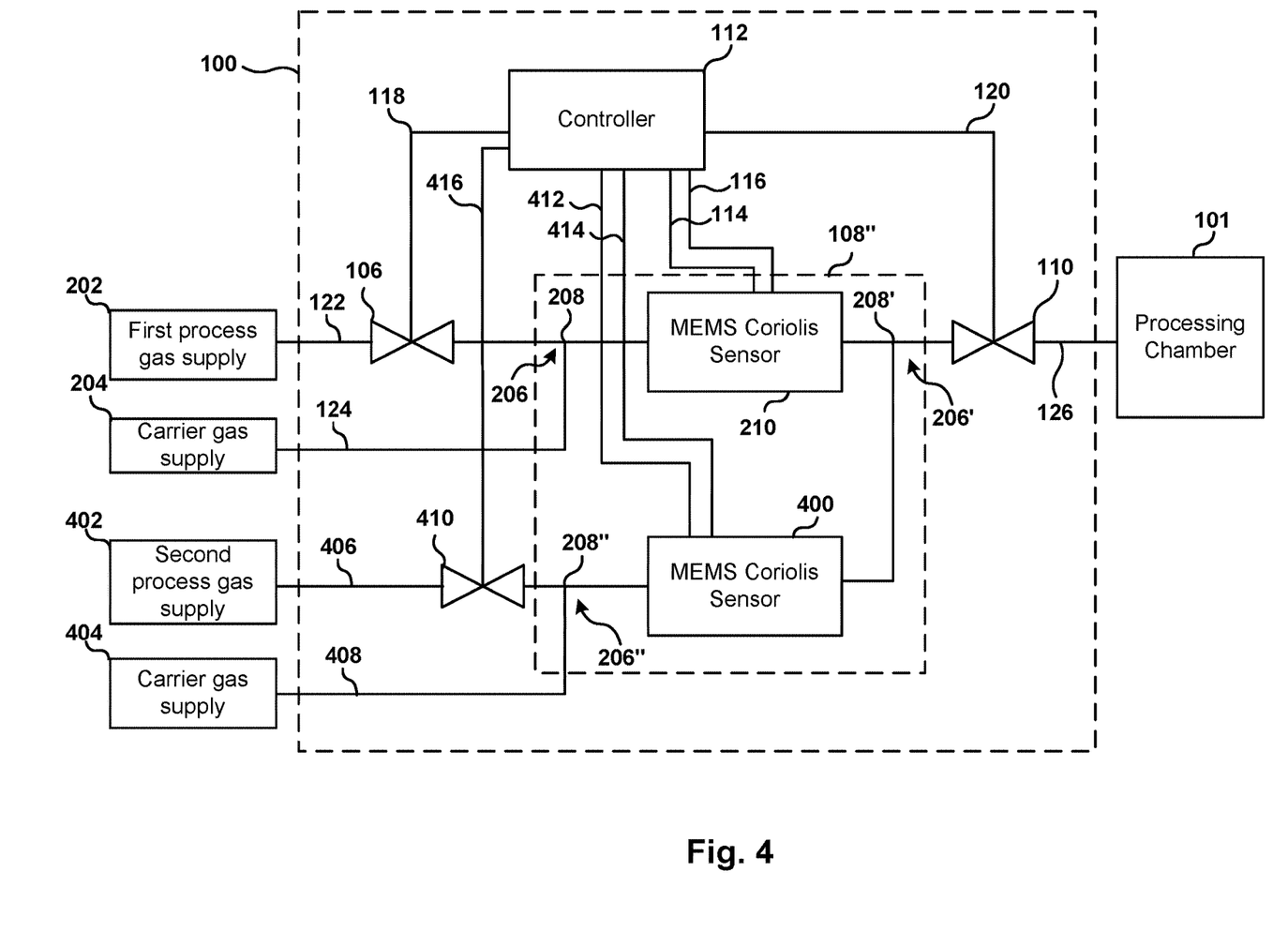
FIG. 4 is a schematic diagram of a system for controlling delivery of a first and second process gas in mixture with carrier gases to a processing chamber using two Coriolis sensors, according to one embodiment.

FIG. 4 is a schematic diagram of a system for controlling delivery of a first and second process gas in mixture with carrier gases to a processing chamber 101 using two Coriolis sensors, according to one embodiment. The MFC 100 shown in FIG. 4 extends the principles and technical advantages of the system shown in FIG. 2 to encompass the precise delivery of two process gasses to the processing chamber 101. The MFC 100 receives a first process gas via flow line 122 from first process gas supply 202 and a first carrier gas via flow line 124 from first carrier gas supply 204. Similar to the MFC 100 shown in FIG. 2, an inlet valve 106 is disposed along flow line 122 for controlling the flow rate of the first process gas. The first process gas and the first carrier gas are mixed at mixing point 206 where a connector 208 couples flow lines 122 and 124. The mixing point 206 and the connector 208 are downstream of the inlet valve 106 and upstream of the MEMS Coriolis sensor 210. The mixture of the first process gas and the first carrier gas enter the MEMS Coriolis sensor 210, which provides a density signal 114 and a flow signal 116 to the controller 112 for the mixture of the first process gas and the first carrier gas.

The MFC 100 shown in FIG. 4 also receives a second process gas via flow line 406 from second process gas supply 402 and a second carrier gas via flow line 408 from second carrier gas supply 404. An inlet valve 410 is shown to be disposed along flow line 406 for controlling the flow rate of the second process gas. The second process gas and the second carrier gas are mixed at mixing point 206" where a connector 208" couples flow lines 406 and 408. The mixing point 206" and the connector 208" are shown to be downstream of the inlet valve 410 and upstream of the MEMS Coriolis sensor 410. The mixture of the second process gas and second carrier gas enters the MEMS Coriolis sensor 400, which provides a density signal 412 and a flow signal 414 for the mixture of the second process gas and the second carrier gas. It is noted here that the second carrier gas may, in some embodiments, be the same as the first carrier gas. For example, in some embodiments, the first carrier gas supply 204 may supply a carrier gas for both the first and second process gases.

The mixture of the first process gas and the first carrier gas and the mixture of the second process gas and the second carrier gas are shown to be mixed at mixing point 206' where connector 208' couples the lines exiting the MEMS Coriolis sensor 210 and the MEMS Coriolis sensor 400. The resulting final mixture will include the first process gas, the second process gas, and the first and second carrier gases if the first and second carrier gases are not the same. If the first and second carrier gases are the same, then the resulting final mixture will include the first and second process gases and the carrier gas. The final mixture of the first and second process gases and the one or two carrier gases flows to the processing chamber 101 via outlet line 126. An outlet valve 110 is disposed along the outlet line 126 for controlling the total flow of the final mixture of the first and second process gases and the one or two carrier gases that exit the MFC 100 and enter the processing chamber 101.

According to the embodiment shown in FIG. 4, the ratio of the first process gas to the first carrier gas may be calculated based on the density signal 114 while the ratio of the second process gas to the second carrier gas may be calculated based on the density signal 412. Additionally, a gas mix ratio of either the first or second process gas with respect to the final mixture may be obtained. For example, the density signal 114 may provide that the first mixture of the first process gas and the first carrier gas has a density of 2 g/L. From equation (3), the fractional density of the first process gas may be calculated to be, for example, y=0.1, while the fractional density of the first carrier gas may be calculated to be x=0.9. As a result, the density of the process gas may be calculated to be 0.2 g/L. Additionally, the density signal 412 may provide that the second mixture of the second process gas and the second carrier gas has a density of 8 g/L. According to equation (3), the fractional density of the second process gas to the second carrier gas may be calculated to be, for example, y=0.2, while the fractional density of the carrier gas would be x=0.8. Thus, the density of the second process gas within the second mixture as well as the final mixture is to be 1.6 g/L. The ratio of the first process gas to the final mixture may be calculated to be (0.2 g/L)/(2 g/L+8 g/L)=0.02. The ratio of the second process gas to the final mixture will also be calculated to be (1.6 g/L)/(2 g/L+8 g/L)=0.16. If either the ratio of the first process gas or the second process gas is higher or lower than a desired ratio, the inlet valves 106 and 410 may be adjusted, respectively, to obtain a desired ratio.

For example, if the ratio of the first process gas is desired to be 0.04 of the final mixture and the ratio of the second process gas is desired to be 0.16 of the final mixture, the controller 112 may send a density signal feedback 118 to inlet valve 106 to increase the flow of the first process gas into MFC 100. The increased flow of the first process gas into the MFC 100 may change the ratio of the second process gas to the final mixture, however. As a result, the controller 112 could calculate a density signal feedback 118 and a density signal feedback 412 that would result in the ratio of the first process gas in the final mixture to be 0.04 while maintaining the ratio of 0.16 for the second process gas in the final mixture.

According to the embodiment shown in FIG. 4, the mass flow rate of the mixture of the first process gas and the first carrier gas is provided by flow signal 116 whereas the mass flow rate of the mixture of the second process gas and the second carrier gas is provided by flow signal 414. For example, the mass flow rate of the mixture between the first process gas and first carrier gas may be calculated from flow signal 116 to be $\dot{m}_1$=0.02 g/min. Moreover, the mass flow rate of the mixture between the second process gas and the second carrier gas may be calculated from flow signal 414 to be $\dot{m}_2$=0.08 g/min. The resulting mass flow rate of the final mixture may be calculated to be $\dot{m}_{total}$=$\dot{m}_1$+$\dot{m}_2$=0.1 g/min. Continuing with the example provided above, the mass flow rate specific to the first process gas may be calculated to be (0.1)(0.02 g/min)=0.002 g/min, or alternatively, (0.02)(0.1 g/min)=0.002 g/min. The mass flow rate specific to the second process gas may calculated to be (0.2)(0.08 g/min)=0.016 g/min, or alternatively, (0.16)(0.1 g/min)=0.016 g/min. If the desired mass flow rate for the first process gas and the second process gas is higher or lower than 0.002 g/min and 0.016 g/min, respectively, then the controller 112 may send a flow signal feedback 120 to reduce or increase the total mass flow rate of the mixture that is allowed through outlet valve 110.

Figure 5A:
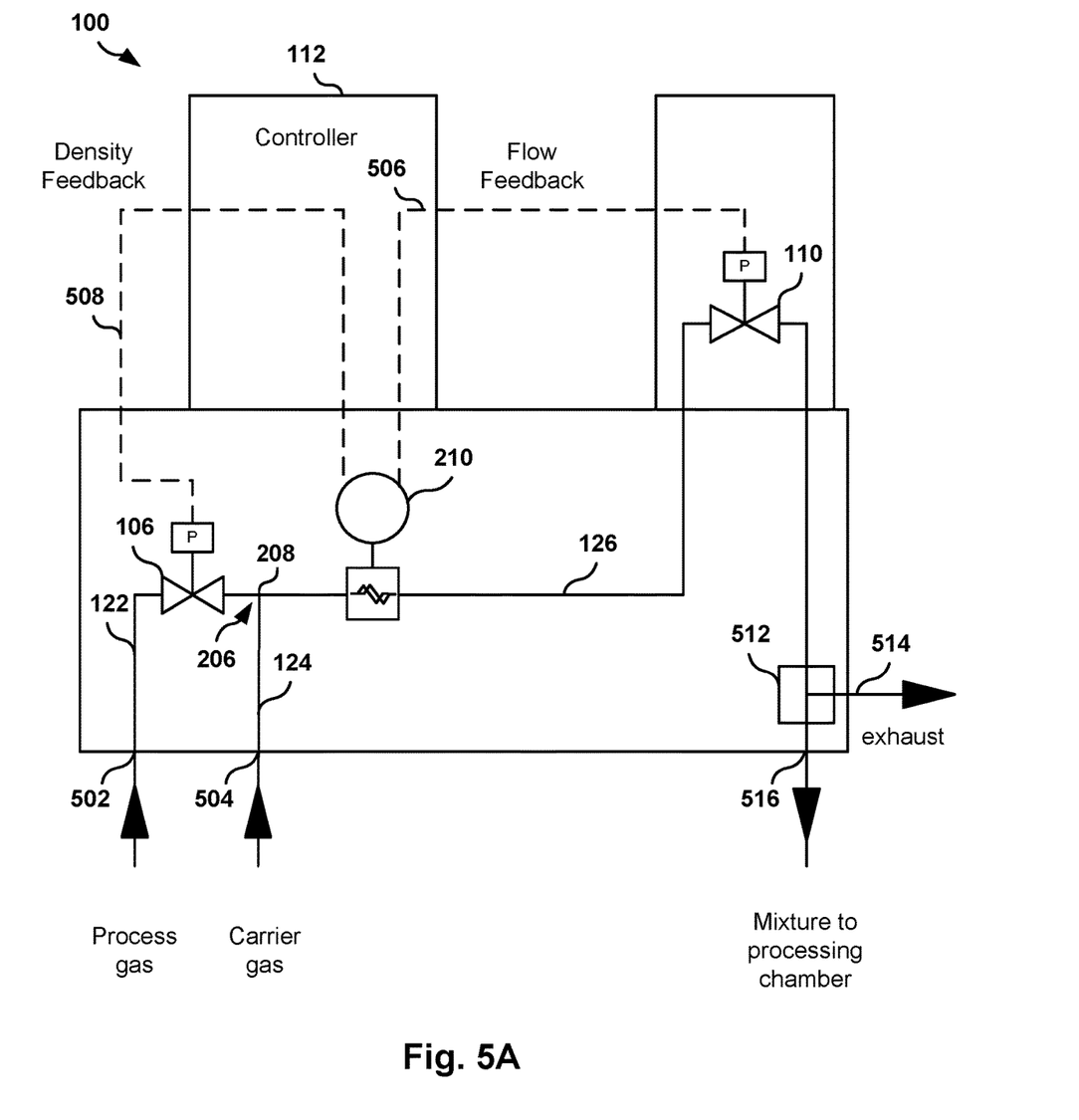
FIG. 5A is a schematic diagram of a mass flow controller for controlling a mass flow rate of a mixture of a process gas and a carrier gas supplied to a processing chamber, according to one embodiment.

FIG. 5A illustrates an additional view of an MFC 100, in accordance with the various embodiments described herein. The MFC 100 includes an inlet 502 for process gas and an inlet 504 for carrier gas. The process gas travels through conduit flow line 122 before reaching mixing point 206 defined by a connector 208. Disposed along flow line 122 is an inlet valve 106 for controlling the flow of the process gas that enters the MFC 100. The carrier gas enters the MFC 100 through inlet 504 and travels through flow line 124 before reaching the mixing point 206. The process gas and the carrier gas become a mixture before entering the MEMS Coriolis sensor 210. The mixture exits the MEMS Coriolis sensor 210 via outlet line 126, which leads to outlet 516. The mixture may then be delivered to a processing chamber that is in fluid communication with the MFC 100. Disposed along the conduit 216 is an outlet valve 116 for controlling the total flow rate of the mixture that exits the MFC 100.

Figure 5B:
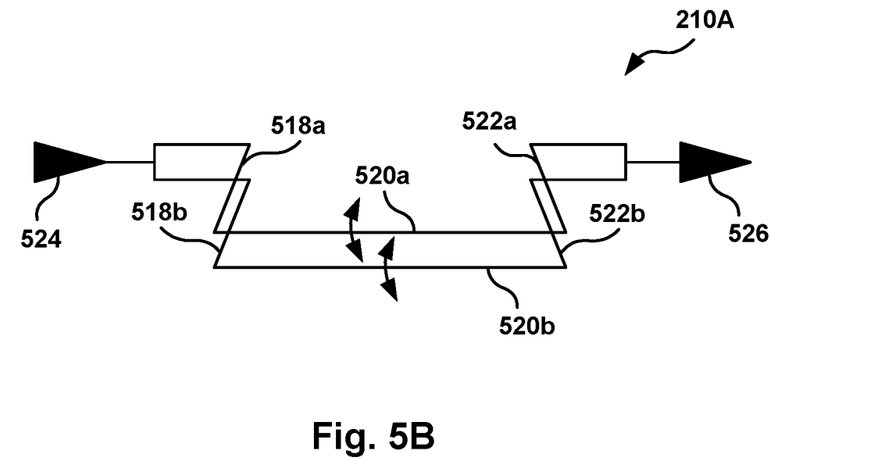
FIGS. 5B and 5C illustrate exemplary embodiments of Coriolis sensors that may be utilized with systems and methods described herein, according to some embodiments.
Figure 5C:
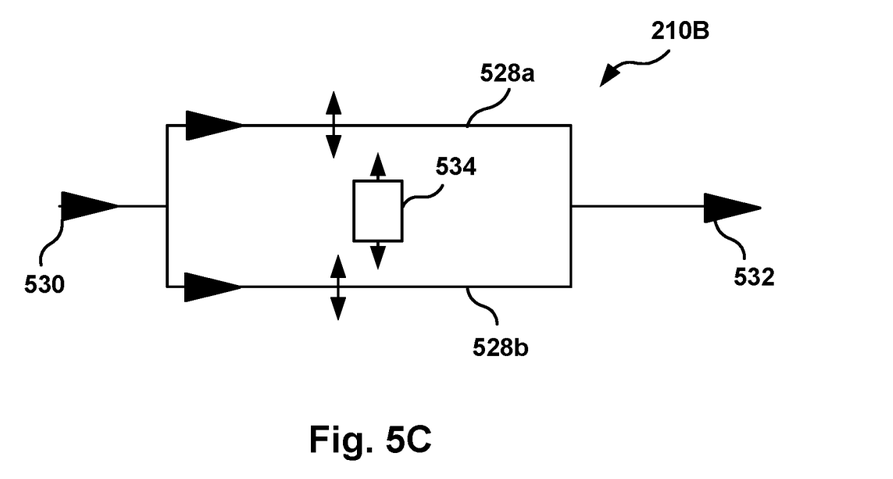

The MEMS Coriolis sensor 210 used in various embodiments described herein may be any type of suitable Coriolis sensor that provides a signal related to density of a measured fluid and a signal related to flow of the measured fluid. Some examples of suitable Coriolis sensor configurations are shown in FIGS. 5B and 5C. The MEMS Coriolis sensor 210 shown in FIG. 5A provides a density feedback 508 that is used to drive or operate the inlet valve 106 for controlling the flow of the process gas that enters the MFC 100. Additionally, the MEMS Coriolis sensor 210 provides a flow feedback 506 that is used to drive or operate the outlet valve 110 for controlling the total flow rate of the mixture that exits the MFC 100.

The MEMS Coriolis sensor 210 includes a tube through which the mixture travels. As noted above, the density signal 506 provides the controller 112 with a signal related to density of the mixture. The density signal 506 is generated by examining a change in the frequency with which the tube of the MEMS Coriolis sensor 210 vibrates when a fluid is introduced to the tube as compared with that when no fluid is the tube. The density signal 506 can be used to calculate the fractional density for either the process gas or the carrier gas within the mixture, which also expresses the gas mix ratio of the mixture. The controller 112 uses the density feedback 508 to adjust the inlet valve 10 until a desired gas mix ratio is achieved.

Additionally, the flow feedback 506 provides the controller 112 with a signal related to the mass flow rate of the mixture as it travels through the MEMS Coriolis sensor 210. The flow signal is generated by examining the phase shift or time delay between an inlet arm and an outlet arm of the tube as the mixture travels through the MEMS Coriolis sensor 210. The flow feedback 506 is used to calculate the mass flow rate of the mixture that travels through the MFC 100. Further, the specific mass flow rate of the process gas or the carrier gas may be determined using the gas mix ratio and the mass flow rate. The controller 112 uses the flow feedback 506 to adjust the outlet valve 110 until a desired mass flow rate for the process gas is achieved.

Also shown in FIG. 5A is an optional switch valve 512 that may be used for switching the flow of the mixture between a line that is delivered to the processing chamber (e.g., through outlet 516) and an exhaust line 514. For certain applications such as atomic layer deposition and atomic layer etching, the switch valve 512 provides an opportunity to pulse the output of MFC 100 while maintaining a small constant or near constant inlet flow of process gas into the MFC 100.

FIG. 5B shows an embodiment of a Coriolis sensor 210A of a curved tube configuration. The Coriolis sensor 210A includes an inlet 524 and an outlet 526 for measuring, for example, a flow mixture of process gas and carrier gas. The flow is split into two tubes, each tube including an inlet portion, 518a and 518b, a central portion, 520a and 520b, and an outlet portion, 522a and 522b. The central portions 520a and 520b are excited to a resonant frequency by an electrostatic, a piezoelectric, or an electromagnetic mechanism and vibrate in a directionality indicated by the double-headed arrows is shown in FIG. 5B.

FIG. 5C shows an additional embodiment of a Coriolis sensor 210B that may be used with the various embodiments of mass flow controllers described herein. The Coriolis sensor 210B includes an inlet 530 and an outlet 532 for measuring, for example, a flow of a mixture of process gas and carrier gas. In this embodiment, the flow is split into two parallel tubes 528a and 528b. The tubes are driven to a resonant frequency by a driving mechanism 534 in a directionality indicated by the double-headed arrows in FIG. 5C. The driving mechanism 534 may use electrostatic, electromagnetic, and piezoelectric forces to drive the tubes, and the changes in frequency experienced by the tubes may be measured electrostatically, electromagnetically, piezoelectrically, or optically.

Figure 6:
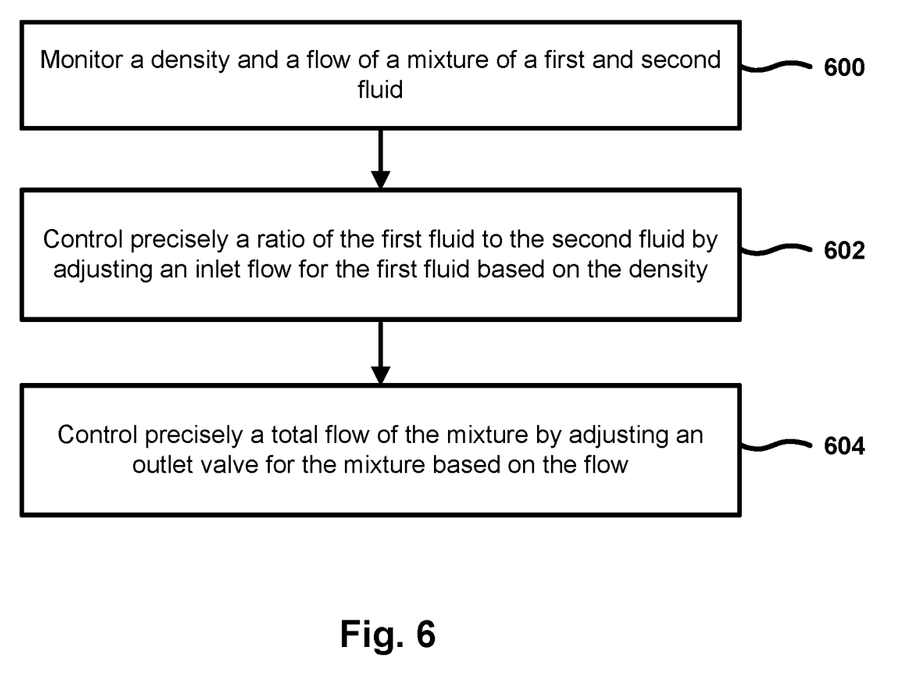
FIG. 6 illustrates an overall flow of a method for controlling delivery of gas using systems described herein, according to one embodiment.

FIG. 6 illustrates an overall flow of a method for controlling a fluid delivery system or a gas delivery system, according to one embodiment. The fluid delivery system may be a mass flow controller and gas mixer as shown in the embodiments of FIGS. 1-3. As used herein, the term fluid is meant to include any matter that is in a liquid state or in a gaseous state. Operation 600 includes monitoring a density and flow of a mixture of first and second fluids with, for example, a Coriolis sensor. In order to monitor the density of the mixture for operation 600, the density signal may be used to calculate the density of the mixture, which may be obtained to a high degree of accuracy (e.g., $10^{-5} \Delta\rho/\rho$). A gas mix ratio may also be derived from the measurement of the density of the mixture, for example, by using equations (3) and (4).

For example, $\rho_{mixture} = x\rho_{carrier} + y\rho_{process}$ of equation (3) may be solved for x and y by obtaining $\rho_{mixture}$ from the density signal, and $\rho_{carrier}$ and $\rho_{process}$ from a look-up table or by solving $$\rho = \frac{P}{R_{sp}T}$$

from equation (4). In other embodiments, $\rho_{carrier}$ and $\rho_{process}$ may be obtained empirically. For example, an inlet valve for the process gas may be shut off such that only carrier gas flows through the Coriolis sensor. The resulting density signal will reflect the density specific to the carrier gas, $\rho_{carrier}$. Similarly, an inlet valve for the carrier gas may be shut off such that only process gas flows through the Coriolis sensor. The resulting density signal will reflect the density specific to the process gas, $\rho_{process}$. Thus, both $\rho_{carrier}$ and $\rho_{process}$ may be obtained empirically in some embodiments for the gas mix ratio calculation.

In order to monitor the flow of the mixture in operation 600, the flow rate may be calculated from a flow signal provided by the Coriolis sensor. The flow signal is based on a phase shift or time lag in vibration between an inlet portion of a tube of the Coriolis sensor and an outlet portion of the tube. For example, with respect to FIG. 5B, the flow signal would be based on a phase shift or time lag between the inlet portion 518a and outlet portion 522a, or between inlet portion 518b and outlet portion 522b. In many circumstances, the phase shift or time lag between inlet portion 518a and outlet portion 522a, and that of inlet portion 518b and 522b will be nearly the same. A flow rate of the mixture would then be calculated by operation 600 by using an equation such as equation (1). The flow rate obtained in operation 600 may be a mass flow rate or a volumetric flow rate. In many embodiments, however, a mass flow rate may be desired.

In operation 602, the method includes controlling the ratio of the first fluid and the second fluid by adjusting an inlet flow of the first fluid based on the density signal. For example, if it is found in operation 600 that the ratio of process gas to carrier gas is greater than a desired ratio, the inlet valve for the process gas may be signaled to reduce the flow of the process gas. The signal to reduce the flow may be calculated from the difference between the desired gas mix ratio and the current or actual gas mix ratio. Thus, if the difference between the desired and the actual gas mix ratio is large, the signal may be operable to reduce the flow by a larger degree than if the difference were smaller. Once an adjustment is made to the inlet valve, the Coriolis sensor will signal that there is a change in density caused by the increased or decreased flow of the process gas. The process may be repeated until the ratio of process gas and carrier gas is at the desired ratio, or within a desired range.

The method proceeds to operation 604, which includes controlling precisely the total flow of the mixture that exits the gas delivery system (e.g., the MFC). As noted above, certain applications of gas delivery for substrate processing require precise control over the flow rate of the process gas that is allowed to enter the processing chamber as well as precise control over the total amount of process gas that is introduced into the processing chamber is desired. This may be true for applications such as atomic layer etching and deposition in which only the top atomic layer of the substrate surface is affected by each step. Operation 604 provides a desired level of precision for the delivery of process gas from the accuracy of the density and flow signals that are obtained from the Coriolis sensor along with precise control over the inlet and outlet valves. For example, the mass flow rate measurement that is provided by the Coriolis sensor is contemplated to be accurate to at least $5 \times 10^{-4} \Delta Q_m/Q_m$.

It is also noted here the accuracy of density and flow measurements are relatively unaffected by the flow rate of the carrier gas that enters the gas delivery system. In most embodiments, the carrier gas flow is relatively stable. However, even if it is not, operation 600 is enabled to provide real time or near real time density and flow signals that account for the non-constant flow of carrier gas. For example, if the flow of carrier gas varies over a period of 60 seconds, the gas mix ratio of process gas to carrier gas will also vary during the same period. However, in some embodiments, operation 600 monitors the density of the mixture that travels through the gas delivery system in real time, and, as a result, can determine at any given point within the 60 seconds what the gas mix ratio of process gas to carrier gas is. Likewise, operation 600 can also determine the mass flow rate of the mixture at any given point within the 60 second period. As a result, the method shown in FIG. 6 can be used to determine the amount of process gas that has been delivered to the processing chamber as well as how much more process gas is desired to be delivered. Thus, the method enables the precise delivery of an amount of process gas into the processing chamber, even when the flow of carrier gas is not constant.

Figure 7:
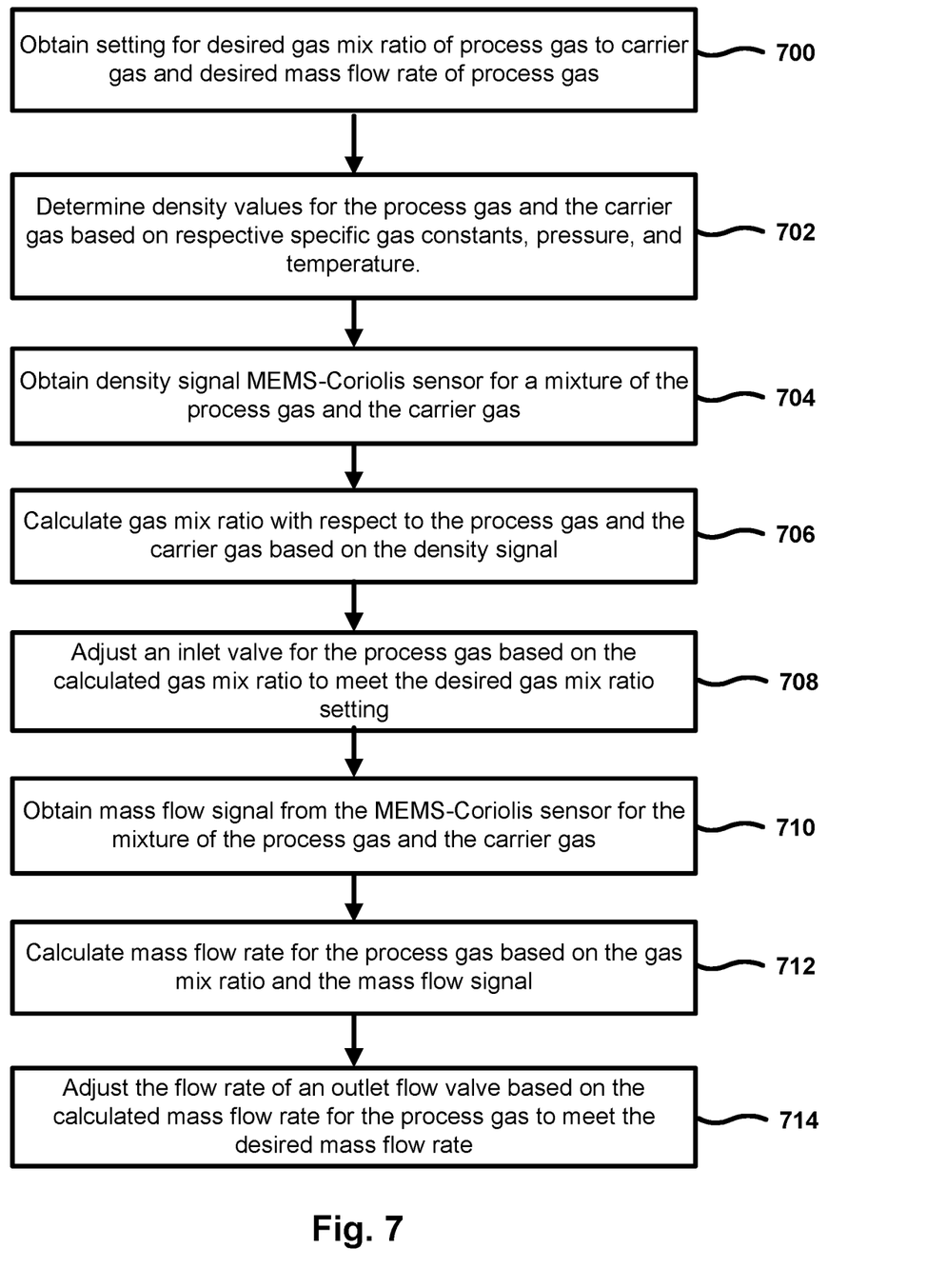
FIG. 7 illustrates an overall flow of a method for controlling delivery of gas using systems described herein, according to an additional embodiment.

FIG. 7 is a flow chart that illustrates the method operations that may be carried out by a mass flow controller, according to one embodiment. In operation 700, settings for the desired gas mix ratio of process gas to carrier gas, as well as the desired setting for the mass flow rate of the process gas, are obtained. These settings may be manually input by a human operator, or they may be calculated or looked up depending upon the substrate processing steps, e.g., recipe, being carried out. In other embodiments, a setting for a total amount of process gas to be delivered to a processing chamber for a given step or treatment may be received. The desired gas mix ratio and the mass flow rate settings may be calculated from the total amount of process gas that is set to be delivered to the processing chamber in operation 700. In addition, operation 700 may also calculate an amount of time to allow the mixture to flow into the processing chamber. For example, if the total amount of process gas that is set to be delivered into the processing chamber is 0.01 grams, and the mass flow rate specific to the process gas is 0.1 gram/minute, then the total amount of time that the mixture should be allowed to enter the processing chamber should be about 6 seconds.

In operation 702, the density values for the process gas and for the carrier gas are determined based on respective specific gas constants, pressure values, and temperature values. These density values may be obtained, for example, by using equation (4). In other embodiments, the density values may be determined empirically by measuring the process gas and the carrier gas individually.

In operation 704, the density signal is obtained from the MEMS Coriolis sensor for a mixture of the process gas and the carrier gas. In some embodiments, the density signal is related to a frequency measurement of a tube of the MEMS Coriolis sensor. Operation 704 is configured to calculate a difference between the current resonant frequency measurement and that of a baseline resonant frequency (e.g., a resonant frequency of tube without any contents). The difference between the current resonant frequency measurement and the baseline resonant frequency is then used to calculate the density of the mixture. In operation 706, a gas mix ratio and/or the fractional density values for the gases are calculated, for example, by using equation (3) along with the density value calculated for the mixture in operation 704. Based upon the gas mix ratio calculation obtained in operation 706, operation 708 serves to adjust the inlet valve that controls the flow rate of process gas that is introduced into the MFC. Operations 704 through 708 may be repeated until the desired gas mix ratio is achieved. In some embodiments, operation 708 may also adjust an inlet valve that controls the inflow of carrier gas in order to obtain the desired gas mix ratio between process gas and carrier gas.

In operation 710, the method includes obtaining a mass flow rate signal from the MEMS Coriolis sensor for determining the mass flow rate of the mixture. As noted above, the mass flow signal may be related to a phase shift or time lag measurement between opposite ends of a vibrating tube of the MEMS Coriolis sensor. The phase shift or time lag measurement is then used by operation 710 to calculate the mass flow rate of the mixture that flows through the MEMS Coriolis sensor. In operation 712 the method calculates the mass flow rate specific for the process gas based on the mass flow rate obtained in operation 710 and the gas mix ratio calculated in operation 706. For example, the mass flow rate specific to the process gas may be calculated by obtaining the product of the total mass flow rate of the mixture and the proportion of process gas to the mixture. Based upon the calculation obtained in operation 712, operation 714 serves to adjust the flow rate of an outlet valve that is output by the MFC and that is delivered to a processing chamber. Operations 710 through 714 may be repeated until the desired mass flow rate specific to the process gas is obtained.

In some embodiments, two mass flow controllers are used to control the flow rate of the process gas and the carrier gas for delivery to processing chambers, one MFC for each of the process and carrier gases. The embodiment shown in FIG. 2 is contemplated to provide additional advantages to systems having an MFC for each gas. For example, the embodiment shown in FIG. 2 is able to control both the gas mix ratio and the mass flow rate of two gases with a single MFC, which reduces cost and footprint of the gas delivery system. It is also contemplated that the embodiment shown in FIG. 2 provides a measurement of the mass flow rate of the process gas (e.g., the low flow gas) that is more accurate than that of the two-MFC configuration.

For example, assume that a desired flow rate of process gas is about 0.1 sccms and that the carrier gas is to be about 10 sccms. Using the two-MFC system, one of the MFCs will be responsible for measuring 0.1 sccms, which may outside of an optimal range in which flow rates can be accurately measured. In contrast, using the embodiment shown in FIG. 2, the MFC 100 essentially measures the 0.1 sccm flow within the mixture having a flow in the range of 10 sccms, which is within a more optimal range of flow rates that can be more accurately measured. As a result, the embodiments such as the one shown in FIG. 2 are able to accurately measure low flows (e.g., lower than about 2 sccms) in a way that multiple MFC systems are not able to do.

It is also contemplated that the embodiments such as the one shown in FIG. 2 allow for a reduction of the delay associated with the time it takes a gas to reach the processing chamber from the output valve of an MFC. For example, the time delay for a gas to reach the processing chamber may be expressed by the following:

$$t \propto \frac{\text{tube length} \times \text{flow rate}}{\text{diameter}^2} \quad (5)$$

In certain embodiments such as those having two MFCs for controlling both the process gas and the carrier gas separately, the tube lengths may be about 100 mm or greater. If the flow of gas is relatively low (e.g., less than 2 sccms), it could take up to 50 seconds for the gas to travel from the output valve of the MFC to the processing chamber. The tube length cannot be made much shorter because the mixing of the gases at the mixing point occurs downstream of the MFCs.

The embodiments described herein and shown, for example, in FIG. 2 are able to shorten the tube length between the outlet valve 110 of the MFC 100 and the processing chamber 101 by up to a factor of about 10 or more. In FIG. 2, for example, the mixing at the mixing point 206 occurs before the gases enter the MEMS Coriolis sensor 210. As a result, the tube length between the outlet valve 110 of the MFC 100 may be reduced such that the time delay is reduced to between about 30 seconds to about 1 second, or between about 20 seconds to about 2 seconds, or between about 10 seconds to about 5 seconds.

Computer programs for controlling delivery of process gas can be written in any conventional computer readable programming language: for example, assembly language, C, C++, Pascal, Fortran or others. Compiled object code or script is executed by the processor to perform the tasks identified in the program.

The system software may be designed or configured in many different ways. For example, various chamber and MFC component subroutines or control objects may be written to control operation of the MFC components necessary to carry out the flow control processes.

With the above embodiments in mind, it should be understood that the embodiments can employ various computer-implemented operations involving data stored in computer systems. These operations are those requiring physical manipulation of physical quantities. Any of the operations described herein that form part of the embodiments are useful machine operations. The embodiments also relates to a device or an apparatus for performing these operations. The apparatus may be specially constructed for the required purpose, such as a special purpose computer. When defined as a special purpose computer, the computer can also perform other processing, program execution or routines that are not part of the special purpose, while still being capable of operating for the special purpose. Alternatively, the operations may be processed by a general purpose computer selectively activated or configured by one or more computer programs stored in the computer memory, cache, or obtained over a network. When data is obtained over a network the data may be processed by other computers on the network, e.g., a cloud of computing resources.

One or more embodiments can also be fabricated as computer readable code on a computer readable medium. The computer readable medium is any data storage device that can store data, which can be thereafter be read by a computer system. Examples of the computer readable medium include hard drives, network attached storage (NAS), read-only memory, random-access memory, CD-ROMs, CD-Rs, CD-RWs, magnetic tapes and other optical and non-optical data storage devices. The computer readable medium can include computer readable tangible medium distributed over a network-coupled computer system so that the computer readable code is stored and executed in a distributed fashion.

Although the method operations were described in a specific order, it should be understood that other housekeeping operations may be performed in between operations, or operations may be adjusted so that they occur at slightly different times, or may be distributed in a system which allows the occurrence of the processing operations at various intervals associated with the processing, as long as the processing of the overlay operations are performed in the desired way.

Although the foregoing embodiments have been described in some detail for purposes of clarity of understanding, it will be apparent that certain changes and modifications may be practiced within the scope of the disclosed embodiments. It should be noted that there are many alternative ways of implementing the processes, systems, and apparatus of the present embodiments. Accordingly, the present embodiments are to be considered as illustrative and not restrictive, and the embodiments are not to be limited to the details given herein.

What is claimed is:

1. A mass flow controller, comprising:
   a first flow line for introducing a process fluid into the mass flow controller;
   an inlet valve disposed along the first flow line for controlling a flow rate of the process fluid;
   a second flow line for introducing a carrier fluid into the mass flow controller, wherein the mass flow controller is connected to receive both the first flow line and the second flow line;
   a micro-electro-mechanical system (MEMS) Coriolis sensor for providing a density signal and a mass flow rate signal for a mixture of the process fluid and the carrier fluid;
   an outlet valve for controlling a mass flow rate of the mixture that is output by the mass flow controller; and
   a controller for operating the inlet valve based on the density signal and for operating the outlet valve based on the mass flow rate signal.

2. The mass flow controller of claim 1, further comprising:
   a connector that joins the first flow line and the second flow line disposed downstream of the inlet valve and upstream of the MEMS Coriolis sensor, the connector mixes the process fluid and the carrier fluid into the mixture.

3. The mass flow controller of claim 1, wherein the process fluid is a process gas and the carrier fluid is a carrier gas.

4. The mass flow controller of claim 1, wherein the flow rate of the process fluid introduced into the mass flow controller is defined by a low flow rate.

5. The mass flow controller of claim 4, wherein the low flow rate is defined by a rate of 2 standard cubic centimeters per minute (sccms) or lower.

6. The mass flow controller of claim 1, wherein the controller is configured to adjust the outlet valve based on the mass flow rate signal to achieve a desired mass flow rate for the mixture.

7. The mass flow controller of claim 1, wherein the controller is configured to calculate a fluid mix ratio of process fluid to carrier fluid, and wherein the controller is further configured to adjust the inlet valve based on the calculated fluid mix ratio to achieve a desired fluid mix ratio.

8. The mass flow controller of claim 7, wherein the controller is further configured to calculate a mass flow rate specific to the process fluid based on the fluid mix ratio and based on the mass flow rate signal, and wherein the controller is further configured to adjust the outlet valve based on the calculated mass flow rate specific to the process fluid to achieve a desired mass flow rate specific to the process fluid.

9. The mass flow controller of claim 1, wherein the mass flow controller is in fluid communication with a processing chamber via the outlet valve such that the mass flow controller controls delivery of the mixture of process fluid and carrier fluid into the processing chamber.

10. A method for controlling a mass flow controller (MFC), comprising:
    receiving, from a Coriolis sensor of the MFC, a density signal and a mass flow rate signal for a mixture of a process fluid and a carrier fluid, the MFC being connected to both a first flow line of the process fluid and a second flow line of the carrier gas;
    calculating a fluid mix ratio of the mixture based on the density signal;
    adjusting a flow rate of the process fluid entering the MFC based on the fluid mix ratio;
    calculating a mass flow rate of the mixture based on the mass flow rate signal; and
    adjusting an output flow rate of the mixture exiting the MFC based on the mass flow rate of the mixture.

11. The method of claim 10, wherein the density signal is associated with a measurement of a change in vibration frequency of a tube of the Coriolis sensor.

12. The method of claim 10, wherein the flow signal is associated with a measurement of a phase shift in vibration frequency between two arms of a tube of the Coriolis sensor.

13. The method of claim 10, wherein said calculating the fluid mix ratio includes determining a density of the process fluid and a density of the carrier fluid.

14. The method of claim 10, further comprising:
    calculating a mass flow rate specific to the process fluid based on the fluid mix ratio and the mass flow rate of the mixture, wherein the adjusting the output flow rate of the mixture is further based on the mass flow rate specific to the process fluid.

15. The method of claim 10, wherein said adjusting the flow rate of the process fluid reduces the flow rate of the process fluid when the fluid mix ratio indicates that a ratio of process fluid to carrier fluid is greater than a desired ratio, and wherein said adjusting the flow rate of the process fluid increases the flow rate of the process fluid when the fluid mix ratio indicates that the ratio of process fluid to carrier fluid is less than the desired ratio.

16. The method of claim 10, wherein said adjusting the output flow rate of the mixture reduces the output flow rate of the mixture when the mass flow rate of the mixture is greater than a desired mass flow rate, and wherein said adjusting the output flow rate of the mixture increases the output flow rate of the mixture when the mass flow rate of the mixture is less than a desired mass flow rate.

17. A mass flow controller, comprising:
- a mixing and sensing module for mixing a process fluid and a carrier fluid into a mixture, the mixing and sensing module provides a density signal and a mass flow rate signal for the mixture, the mixing and sensing module being connected to both a first flow line of the process fluid and a second flow line of the carrier gas;
- an inlet valve for controlling a flow rate of process fluid entering the mixing and sensing module;
- an outlet valve for controlling an output flow rate of the mixture exiting the mixing and sensing module; and
- a controller for calculating a fluid mix ratio of process fluid to carrier fluid based on the density signal and for calculating a mass flow rate of the mixture based on the mass flow rate signal for the mixture, wherein the controller is configured for adjusting the inlet valve based on the fluid mix ratio and for adjusting the outlet valve based on the mass flow rate of the mixture.

18. The mass flow controller of claim 17, wherein the controller is further configured to calculate a mass flow rate specific to the process fluid based on the fluid mix ratio and the mass flow rate of the mixture, and wherein said adjusting the outlet valve is further based on the mass flow rate specific to the process fluid.

19. The mass flow controller of claim 17, wherein the mixing and sensing module includes a Coriolis sensor for providing the density signal and the mass flow rate signal for the mixture, the mixing and sensing module further includes a connector disposed downstream of the inlet valve and upstream of the Coriolis sensor, the connector defines a mixing point for mixing the process fluid and the carrier fluid into the mixture.

20. The mass flow controller of claim 17, wherein the mass flow controller is part of a system, the system further comprising a processing chamber for processing a substrate using the mixture output by the mass flow controller.

* * * * *